United States Patent
Ngo et al.

(10) Patent No.: US 6,461,161 B1
(45) Date of Patent: Oct. 8, 2002

(54) TOOTH SURFACE TREATMENT METHOD

(75) Inventors: Hien Ngo, Athelstone; Geoffrey M. Knight, Brighton; Graham George Craig, Balgowlah, all of (AU); Toshihiro Sekiguchi, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/864,250

(22) Filed: May 25, 2001

(51) Int. Cl.⁷ .................................................. A61C 5/00
(52) U.S. Cl. .................................................. 433/217.1
(58) Field of Search ........................ 433/217.1, 216, 433/215

(56) References Cited

U.S. PATENT DOCUMENTS

| | | | | |
|---|---|---|---|---|
| 4,012,839 A | * | 3/1977 | Hill ......................... | 433/217.1 |
| 5,688,492 A | * | 11/1997 | Galley et al. ................ | 424/49 |
| 6,306,371 B1 | * | 10/2001 | Wong et al. .................. | 424/49 |

* cited by examiner

Primary Examiner—John J. Wilson
Assistant Examiner—Melba Bumgarner
(74) Attorney, Agent, or Firm—Oblon, Spivak, McClelland, Maier & Neustadt, P.C.

(57) ABSTRACT

There is provided a tooth surface treatment method, which enables one to effectively inhibit the progress of dental caries without impairing the aesthetics. The tooth surface treatment method of the invention includes applying a solution comprising a silver compound in an affected part of a tooth and then applying a solution comprising at least one compound selected from the group of sodium chloride, sodium bromide, sodium iodide, potassium chloride, potassium bromide, potassium iodide, magnesium chloride, magnesium bromide, magnesium iodide, calcium chloride, calcium bromide, calcium iodide thereto. It is preferred that a concentration of silver compound in the solution thereof is 2 to 75% by weight and that a concentration of at least one compound selected from the group of sodium chloride, sodium bromide, sodium iodide, potassium chloride, potassium bromide, potassium iodide, magnesium chloride, magnesium bromide, magnesium iodide, calcium chloride, calcium bromide, calcium iodide in the solution thereof is 1 to 50% by weight.

5 Claims, No Drawings

TOOTH SURFACE TREATMENT METHOD

BACKGROUND OF THE INVENTION

1. Field of the Invention

The present invention relates to a tooth surface treatment method for the inhibition of the progress of dental caries without impairing aesthetics.

2. Description of the Conventional Art

It is considered that about a half of causes for which teeth are lost are because of dental caries. Therefore, it is important to remedy and prevent the dental caries, and various remedy methods have hitherto been developed. In recent years, there has been developed a remedy method in which, even in a state where dental remedy treatment equipments that have hitherto been considered to be necessary in the operative dentistry of the conventional art, such as tooth cutting turbines and electrical equipments, is not available, the remedy of a dental caries for conservation of the tooth can be performed, called "ART" (Atraumatic Restorative Treatment).

In accordance with a basic remedy method of ART, a saliva in a diseased part is wiped out; a dental plaque is removed; a tooth surface is dried; an enamel is cut off by hand instruments such as an excavator, to form a cavity; an enamel piece in the cavity is removed; a dentin that has become soft by the dental caries is removed by using an excavator; the cavity is washed with water; if desired, a tooth surface processing agent or the like is applied; and a glass ionomer cement having a high biocompatibility and a caries preventing function due to sustained fluorine-releasing properties, is filled, thereby completing the treatment. Since ART can be effected by using simple hand instruments and a dental filling material, it is possible to implement the remedy of dental caries even in an area where specific dental equipments are not provided, or electrical supply is not sufficient.

However, in this ART, since it is characterized in that a turbine or the like is not used in cutting the tooth, and the dentin that has become soft by the dental caries is cut by using hand instruments such as an excavator, it was difficult to completely remove the dental caries from the tooth. For this reason, it is feared that the progress of the remained dental caries after the remedy. Thus, a new tooth surface treatment method is necessary.

SUMMARY OF THE INVENTION

An object of the invention is to provide a tooth surface treatment method upon which an effective inhibition for the progress of a dental caries remained on a tooth surface, and which is particularly suitable for ART.

We, the present inventors made extensive and intensive investigations in order to achieve the above-described object and studied a tooth surface treatment method in which a silver compound generally used as an inhibition for progress of dental caries is applied for the purpose of inhibition for the progress of a dental caries remains on a tooth surface, or other methods. As a result, they have found the following matter. That is, after the silver compound has been applied in a cavity, it becomes black silver oxide by oxidation, whereby the tooth is discolored black. Accordingly, when a dental filling material having high transparency, such as glass ionomer cements, is laminated thereon, there remained a problem that the color tone of the glass ionomer cement is inclined to black, thereby remarkably reducing its aesthetics. However, the inventors paid attention to the point that when the silver compound is applied, and a surface treatment with a specific compound is then implemented, sparingly soluble silver phosphate is formed on the tooth surface by silver compound and exert a protein of the dentin to form silver protein, thereby immobilizing the affected dentin; and thereafter, a part of silver liberated on the tooth surface, other than silver protein, is chemically removed as other silver compound from the dentin due to specific compound applied on the tooth surface, whereby not only the effective inhibition for the progress of the dental caries, but also the dentin is free from being colored black due to silver oxide, leading to accomplishment of the invention.

That is, the tooth surface treatment method according to the present invention is a tooth surface treatment method comprising applying a solution comprising a silver compound in an affected part of a tooth and then applying a solution comprising at least one compound selected from the group of sodium chloride, sodium bromide, sodium iodide, potassium chloride, potassium bromide, potassium iodide, magnesium chloride, magnesium bromide, magnesium iodide, calcium chloride, calcium bromide, calcium iodide thereto. Particularly, it is preferred that a concentration of silver compound in the solution is 2 to 75% by weight; and that a concentration of at least one compound selected from the group of sodium chloride, sodium bromide, sodium iodide, potassium chloride, potassium bromide, potassium iodide, magnesium chloride, magnesiumbromide, magnesium iodide, calcium chloride, calcium bromide, calcium iodide in the solution is 1 to 50% by weight.

DETAILED DESCRIPTION OF THE INVENTION

The solution comprising a silver compound that is used in the invention is not particularly limited so far as it is a solution having silver compound dissolved therein. But, since the treatment according to the invention is carried out in a mouth, a solvent is usually water or ethanol. Examples of a silver compound, which is used the diamine silver fluoride, silver nitrate, silver fluoride, silver tetra fluoroborate, silver salfate, silver carbonate. A concentration of silver compound in the solution is preferably 2 to 75% by weight, which is a concentration of silver compound in the solution generally used in the dentistry (for example, a trade name: Saforide, made by Bee Brand Medico Dental Co., Ltd.). When the concentration of silver compound in the solution is less than 2% by weight, the effect for inhibiting the dental caries is hardly provided. On the other hand, when it exceeds 75% by weight, as the solution comprising a silver compound is used in a mouth, the characteristics by silver is not particularly improved.

The solution comprising at least one compound selected from the group of sodium chloride, sodium bromide, sodium iodide, potassium chloride, potassium bromide, potassium iodide, magnesium chloride, magnesium bromide, magnesium iodide, calcium chloride, calcium bromide, calcium iodide that is used in the invention a solution having selected compounds dissolved therein. But, since the treatment according to the invention is carried out in a mouth, a solvent is usually water or ethanol. A concentration of at least one compound selected from the group of sodium chloride, sodium bromide, sodium iodide, potassium chloride, potassium bromide, potassium iodide, magnesium chloride, magnesium bromide, magnesium iodide, calcium chloride, calcium bromide, calcium iodide in the solution is preferably 1 to 50% by weight, which is a concentration of selected compounds in the solution generally used as a medicine (for example, a trade name: Diluted Iodine Tincture, made by SSP Co., Ltd.). When the concentration of at least one compound selected from the group of sodium chloride, sodium bromide, sodium iodide, potassium chloride, potassium bromide, potassium iodide,. magnesium chloride, magnesium bromide, magnesium iodide, calcium chloride, calcium bromide, calcium iodide in the solution is less than 1% by weight, the effect for removing silver formed on the cavity surface is hardly provided. On the other hand, when it exceeds 50% by weight, as the comprising selected compounds in the solution is used in a mouth, it is feared that the irritation tends to increase during contact with portions other than the tooth, such as an oral mucosa.

Next, the tooth surface treatment method according to the invention will be described. Stains, such as accretions, in a portion from which the dental caries has been removed by means of ART or the like, are washed with water; a tooth to be applied is isolated by using a moistureproof material such as a cotton roll, with the tooth in which an affected part to be applied is present being positioned as a center; a saliva is removed by using a cotton ball or the like; and the affected part is dried by air. Then, a few drops of the solution comprising a silver compound are immersed into a small cotton ball and applied in the affected part, followed by washing the inside of the mouth with water. If desired, the foregoing treatment is repeated several times, and the affected part is then dried. Thereafter, a few drops of the solution comprising the selected compounds are immersed into a small cotton ball and applied in the affected part, followed by washing the inside of the mouth with water.

The tooth surface treatment method according to the invention can be used not only for prevention of secondary dental caries because of the effect for inhibiting the dental caries after the remedy of dental caries upon application of ART on the cavity surface, etc. but also for the remedy of a root canal, the remedy of dentinal hyperesthesia, the inhibition of dental caries progress of deciduous teeth, etc., which have hitherto been carried out by using a silver compound. In addition, according to the tooth surface treatment of the invention, since the tooth after the treatment does not cause discoloration, as a matter of course, it can be used for inhibiting the dental caries on permanent teeth, to which silver compound has hitherto been unable to apply.

The tooth surface treatment method according to the invention will be described in more detail with reference to the following Examples. But, it should not be construed that the invention is limited thereto.

Preparation of Solutions Comprising a Silver Compound

A diamine silver fluoride solution 1 was prepared by mixing 27% by weight of diamine silver fluoride into water.

Also, a diamine silver fluoride solution 2 was prepared by mixing 10% by weight of diamine silver fluoride into ethanol.

Preparation of Solution Comprising Selected Compounds

Apotassium iodide solution 1 was prepared by mixing 28% by weight of potassium iodide into a 70% by volume aqueous solution of ethanol.

Also, a potassium iodide solution 2 was prepared by mixing 10% by weight of potassium iodide into water.

EXAMPLE 1

In a tooth crown part of a maxillary left central incisor, was formed a class V cavity having a diameter of about 3 mm and a depth of about 2 mm by means of a hoe and an excavator. After washing with water, a tooth to be treated was isolated by using a cotton roll,. with the tooth being positioned as a center; a saliva was removed by using a cotton ball; and the cavity as an affected part was dried by air. Then, a few drops of the diamine silver fluoride solution 1 were immersed into a small cotton ball and applied in the cavity, and the inside of the mouth was washed with water, followed by drying the cavity. Thereafter, a few drops of the potassium iodide solution 1 were immersed into a small cotton ball and applied in the affected part; the inside of the mouth was washed with water; the cavity was filled with a glass ionomer cement (a trade name: Fuji IX, made by GC Corporation) in a customary manner; and finish polishing was carried out, thereby completing the operation. The progress after the operation was good, and the cavity was not changed black, so that the color tone of the glass ionomer cement was not influenced. Further,even after lapsing 6 months, no secondary dental caries was observed.

EXAMPLE 2

In a tooth crown part of a maxillary left central incisor, was formed a class V. cavity having a diameter of about 3 mm and a depth of about 2 mm by means of a hoe and an excavator. After washing with water, a tooth to be treated was isolated by using a cotton roll, with the tooth being positioned as a center; a saliva was removed by using a cotton ball; and the cavity as an affected part was dried by air. Then, a few drops of the diamine silver fluoride solution 2 were immersed into a small cotton ball and applied in the cavity, and the inside of the mouth was washed with water, followed by drying the cavity. Thereafter, a few drops of the potassium iodide solution 2 were immersed into a small cotton ball and applied in the affected part; the inside of the mouth was washed with water; the cavity was filled with a glass ionomer cement (a trade name: Fuji IX, made by GC Corporation) in a customary manner; and finish polishing was carried out, thereby completing the operation. The progress after the operation was good, and the cavity was not changed black, so that the color tone of the glass ionomer cement was not influenced.

Further, even after lapsing 6 months, no secondary dental caries was observed.

EXAMPLE 3

A dental plaque generated on a surface of a maxillary left first molar of deciduous teeth was removed and washed with water; the tooth to be treated was isolated by using a cotton roll, with the tooth being positioned as a center; a saliva was removed by using a cotton ball; and the dental caries portion as an affected part was dried by air. Then, a few drops of a commercially available diamine silver fluoride solution (a trade name: Saforide, made by Toyo Seika Co., Ltd.) (a concentration of diamine silver fluoride: 38% by weight) were immersed into a small cotton ball and applied in the dental caries portion, and the inside of the mouth was washed with water, followed by drying the dental caries portion. Thereafter, a few drops of a commercially available potassium iodide solution (a trade name: Diluted Iodine Tincture, made by SSP Co., Ltd.) (a concentration of potassium iodide: 40% by weight) were immersed into a small cotton ball and applied in the dental caries portion; and the inside of the mouth was washed with water, thereby completing the operation. The progress after the operation was good, and the tooth surface was not changed black, and the aesthetics were good. Further, even after lapsing 6 months, no secondary dental caries was observed.

As is evident from the foregoing Examples, it has been confirmed that the tooth surface treatment method according to the invention enables one to effectively inhibit the progress of dental caries without impairing the aesthetics.

In the light of the above, the tooth surface treatment method according to the invention is a tooth surface treatment method capable of effectively inhibiting the progress of dental caries and being free from a phenomenon in which a: dentin after the remedy is discolored black by silver oxide. Further, the tooth surface treatment method according to the invention can be used not only for prevention of secondary dental caries because of the effect for inhibiting the dental caries after the remedy of dental caries upon application of ART on the cavity surface, etc. but also for the remedy of a root canal, the remedy of dentinal hyperesthesia, the inhibition of caries progress of deciduous teeth, etc., which have hitherto been carried out by using a solution comprising a silver compound. In addition, according to the tooth surface treatment of the invention, since the tooth after the treatment does not cause discoloration, as a matter of course, it can be used for inhibiting the dental caries on permanent teeth, to which silver compound has hitherto been unable to apply. Accordingly, the invention greatly contributes to the dental remedy.

While the invention has been described in detail and with reference to specific embodiments thereof, it will be apparent to one skilled in the art that various changes and modifications can be made therein without departing from the spirit and scope thereof.

What is claimed is:

1. A tooth surface treatment method comprising applying a solution comprising a silver compound in an affected part of a tooth and then applying a solution comprising at least one compound selected from the group consisting of sodium chloride, sodium bromide, sodium iodide, potassium chloride, potassium bromide, potassium iodide, magnesium chloride, magnesium bromide, magnesium iodide, calcium chloride, calcium bromide, and calcium iodide thereto.

2. The tooth surface treatment method as claimed in claim 1, wherein a concentration of silver compound in the solution is 2 to 75% by weight.

3. The tooth surface treatment method as claimed in claim 2, wherein a concentration of at least of one compound selected from the group consisting of sodium chloride, sodium bromide, sodium iodide, potassium chloride, potassium bromide, potassium iodide, magnesium chloride, magnesium bromide, magnesium iodide, calcium chloride, calcium bromide, and calcium iodide in the solution is to 50% by weight.

4. The tooth surface treatment method as claimed in claim 1, wherein a concentration of at least of one compound selected from the group consisting of sodium chloride, sodium bromide, sodium iodide, potassium chloride, potassium bromide, potassium iodide, magnesium chloride, magnesium bromide, magnesium iodide, calcium chloride, calcium bromide, and calcium iodide in the solution is 1 to 50% by weight.

5. The tooth surface treatment method as claimed in any one of claims 1 to 4, wherein a silver compound is at least one selected from the group consisting of diamine silver fluoride, silver nitrate, silver fluoride, silver tetra fluoroborate, and silver carbonate.

* * * * *